(12) United States Patent
Rashidi (10) Patent No.: US 8,000,764 B2
(45) Date of Patent: *Aug. 16, 2011

(54) ELECTROPHYSIOLOGY/ABLATION CATHETER HAVING SECOND PASSAGE

(75) Inventor: Rassoll Rashidi, Lakewood, OH (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1172 days.

This patent is subject to a terminal disclaimer.

(21) Appl. No.: 11/730,160

(22) Filed: Mar. 29, 2007

(65) Prior Publication Data

US 2007/0244537 A1 Oct. 18, 2007

Related U.S. Application Data

(60) Continuation-in-part of application No. 10/784,512, filed on Feb. 23, 2004, now Pat. No. 7,218,958, and a continuation-in-part of application No. 10/260,242, filed on Sep. 30, 2002, which is a division of application No. 09/232,866, filed on Jan. 15, 1999, now abandoned, which is a continuation-in-part of application No. 08/880,080, filed on Jun. 20, 1997, now Pat. No. 5,861,024.

(51) Int. Cl.
*A61B 5/04* (2006.01)
*A61B 18/14* (2006.01)
(52) U.S. Cl. .......................... 600/374; 600/381; 606/41
(58) Field of Classification Search .................. 600/374; 607/122; 606/41
See application file for complete search history.

(56) References Cited

U.S. PATENT DOCUMENTS

| | | |
|---|---|---|
| 3,190,286 A | 6/1965 | Stokes |
| 3,416,531 A | 12/1968 | Edwards |
| 3,521,620 A | 7/1970 | Cook |
| 3,605,725 A | 9/1971 | Bentov |
| 3,906,938 A | 9/1975 | Fleischhacker |
| 4,559,951 A | 12/1985 | Dahl et al. |
| 4,920,980 A | 5/1990 | Jackowski |
| 4,960,134 A | 10/1990 | Webster, Jr. |
| 5,108,368 A | 4/1992 | Hammerslag et al. |
| 5,125,896 A | 6/1992 | Hojeibane |
| 5,156,151 A | 10/1992 | Imran |
| 5,170,803 A | 12/1992 | Hewson et al. |
| 5,203,772 A | 4/1993 | Hammerslag et al. |
| 5,254,088 A | 10/1993 | Lundquist et al. |
| 5,273,535 A | 12/1993 | Edwards et al. |
| 5,279,299 A | 1/1994 | Imran |
| 5,318,525 A | 6/1994 | West et al. |
| 5,325,845 A | 7/1994 | Adair |
| 5,342,299 A | 8/1994 | Snoke et al. |
| 5,383,852 A | 1/1995 | Stevens-Wright |
| 5,415,633 A | 5/1995 | Lazarus et al. |
| 5,454,370 A | 10/1995 | Avitall |
| 5,462,527 A | 10/1995 | Stevens-Wright et al. |
| 5,465,717 A | 11/1995 | Imran et al. |
| 5,478,330 A | 12/1995 | Imran et al. |

(Continued)

*Primary Examiner* — Lee S Cohen
(74) *Attorney, Agent, or Firm* — Wiley Rein LLP (57) ABSTRACT

A deflectable tip cardiac electrophysiology/ablation lumen catheter includes first and second passages, one of which communicates with an inflatable member or balloon. The second passage terminates in an opening or port downstream of the inflatable member. The second passage is adapted to introduce a liquid during an electrophysiology study while the inflatable member prevents backflow of an injected liquid or dye and blood, or is adapted to alternatively receive a guide wire or other medical device therethrough.

24 Claims, 5 Drawing Sheets

U.S. PATENT DOCUMENTS

| | | |
|---|---|---|
| 5,487,757 A | 1/1996 | Truckai et al. |
| 5,492,131 A | 2/1996 | Galel |
| 5,531,676 A | 7/1996 | Edwards et al. |
| 5,549,542 A | 8/1996 | Kovalcheck |
| 5,552,713 A | 9/1996 | Rashidi |
| 5,562,619 A | 10/1996 | Mirarchi et al. |
| 5,588,964 A | 12/1996 | Imran et al. |
| 5,611,777 A | 3/1997 | Bowden et al. |
| 5,656,029 A | 8/1997 | Imran et al. |
| 5,656,030 A | 8/1997 | Hunjan et al. |
| 5,662,606 A | 9/1997 | Cimino et al. |
| 5,702,433 A | 12/1997 | Taylor et al. |
| 5,715,817 A | 2/1998 | Stevens-Wright et al. |
| 5,735,846 A | 4/1998 | Panescu et al. |
| 5,807,249 A | 9/1998 | Qin et al. |
| 5,853,409 A | 12/1998 | Swanson et al. |
| 5,861,024 A | 1/1999 | Rashidi |
| 5,891,095 A | 4/1999 | Eggers et al. |
| 5,935,102 A | 8/1999 | Bowden et al. |
| 5,944,690 A | 8/1999 | Falwell et al. |
| 5,987,344 A | 11/1999 | West |
| 6,183,463 B1 | 2/2001 | Webster, Jr. |
| 6,221,070 B1 | 4/2001 | Tu et al. |
| 6,272,371 B1 | 8/2001 | Ben-Haim |
| 6,325,797 B1 | 12/2001 | Stewart et al. |
| 6,485,455 B1 * | 11/2002 | Thompson et al. ........ 604/95.04 |
| 7,218,958 B2 * | 5/2007 | Rashidi ........................ 600/374 |
| 2002/0065514 A1 | 5/2002 | Rashidi |
| 2003/0109778 A1 | 6/2003 | Rashidi |
| 2004/0215139 A1 | 10/2004 | Cohen |

* cited by examiner

ELECTROPHYSIOLOGY/ABLATION CATHETER HAVING SECOND PASSAGE

CROSS-REFERENCE TO RELATED APPLICATIONS

This application is a continuation-in-part of U.S. application Ser. No. 10/784,512, filed 23 Feb. 2004, now U.S. Pat. No. 7,218,958. This application is also a continuation-in-part of U.S. application Ser. No. 10/260,242, filed 30 Sep. 2002, now pending, which is a division of U.S. application Ser. No. 09/232,866, filed 15 Jan. 1999, abandoned, which is a continuation-in-part of U.S. application Ser. No. 08/880,080, filed 20 Jun. 1997, now U.S. Pat. No. 5,861,024. The foregoing are hereby incorporated by reference in their entirety as though fully set forth herein.

BACKGROUND OF THE INVENTION a. Field of the Invention

The present invention relates to catheters employed for diagnostic and/or therapeutic procedures in medicine, more specifically in minimally invasive cardiac electrophysiology studies and/or cardiac ablation procedures.

b. Background Art

It is known from the inventors' prior patents and pending applications to provide a pair of tension and compression members (such as push/pull wires) that cooperate to selectively actuate a distal end of a catheter. The distal end typically carries axially-spaced electrodes which, when located in the body passage such as the heart, monitor and record intra-cardiac electrical signals during desired studies or intracardiac mapping procedure. As is known, the electrodes conduct the cardiac electrical signals to monitoring and recording devices. In addition, the electrodes may be used to deliver electrical energy to selectively destroy a site of cardiac tissue that causes an arrhythmia or abnormality in the heart rhythm.

It is important for these types of procedures that wires extending through the catheter for connection with the electrode be of sufficient size to carry desired electrical energy levels to perform these procedures. It is also important that a distal portion of the catheter be able to deflect into a variety of configurations, typically curved configurations having selective radii of curvature in response to actuation from a catheter handle. U.S. Pat. Nos. 5,552,713 and 5,861,024 are commonly owned by the assignee of the present application and show and describe in detail preferred catheter embodiments of this type. The disclosure and details of these patents are expressly incorporated herein by reference. The actuating mechanism described in the patents is ergonomic, easy to operate, requires a relatively low force to form a desired curvature of the catheter distal portion, allows a comfortable range of displacement of the actuator to provide a full range of curvature formation of the catheter distal portion, and permits for curvature formation and curvature retention by a single action of the physician's hand. These desired features are all achieved through side-by-side longitudinal reciprocation of tension/compression members that cooperate to provide simultaneous tension in one member or wire, and compression in the other member or wire. The tension/compression members preferably have a generally circular cross-section throughout a major portion of their length and a generally flattened, ribbon-like configurations adjacent the distal portion of the catheter. A kinematic junction is provided on the ribbon-like portions of the tension/compression members. Bi-directional curvature or lateral deflection is thus provided by employing tension/compression members without the need of a compression strut in the distal portion. Typical dimensions of a catheter casing, electrodes, and diametrical curvature upon actuation are set forth in greater detail in commonly owned U.S. patent application Ser. No. 09/726,235, (Publication No. US-2002-0065514-A1, published May 30, 2002), the details of which are also incorporated herein by reference.

It is known from U.S. Pat. No. 6,325,797 to use an inflatable balloon that is selectively pressurized from an associated liquid source. A lumen is formed within the catheter and carries the liquid, such as saline, to the balloon. In this manner, the balloon is selectively inflated to engage the inner wall of an intracardiac vessel, for example the pulmonary vein wall.

However, a need exists for an electrophysiology lumen catheter that provides effective minimally invasive cardiac diagnostic electrophysiology and/or cardiac ablation procedures, that also provides a flexible liquid delivery tube within the shaft of the catheter, and still maintains all of the benefits of bi-directional deflection and curvature configurations.

BRIEF SUMMARY OF THE INVENTION

According to one embodiment of the invention, an electrophysiology/ablation lumen catheter includes: an elongated flexible body having a proximal end and a series of spaced electrodes disposed adjacent a distal end thereof; a pair of tension/compression members extending through the body for selectively deflecting at least the distal end of the body; an electrical lead connected to each of the electrodes and extending through the body to adjacent the proximal end thereof, the leads adapted for external connection thereof; an actuator operatively connected to the tension/compression members and operable upon movement to effect lateral displacement of the distal end; an inflatable member operatively extending from an outer surface of the body when inflated; a first passage extending through the body adapted to supply an associated liquid therethrough to the inflatable member; and a second passage that communicates with an opening in the body located on the distal end side of the inflatable member. In some embodiments of the invention, the opening is located at a terminus or tip of the distal end, while in other embodiments of the invention, the opening is located inwardly therefrom, between the distal end and the inflatable member. The second passage may be used to deliver liquid or a medical device to a body cavity on the distal side of the inflatable member. Further, it is contemplated that the catheter may be advanced along a guidewire passing through the second passage.

In another embodiment of the invention, an electrophysiology/ablation lumen catheter includes: an elongated flexible body having a proximal end and at least one electrode disposed adjacent a distal end thereof; a catheter deflection assembly disposed in the body, wherein the catheter deflection assembly includes a pair of flexible members disposed substantially side-by-side within the body; an electrical lead connected to each of the electrodes and extending through the body to adjacent the proximal end thereof, the lead adapted for external connection thereof; an actuator connected adjacent the proximal end of the catheter deflection assembly and operable upon movement to effect lateral displacement of the distal end; an inflatable member operatively extending from an outer surface of the body when inflated; a first passage extending through the body adapted to supply an associated liquid therethrough to the inflatable member; and a second passage that communicates with an opening in the body located on the distal end side of the inflatable member. The flexible members may extend through the body from a point of attachment adjacent the distal end to the proximal end such that the deflection assembly may move the distal end in a plane substantially normal to a longitudinal extend of the catheter. Typically, tensioning of one of the pair of flexible members will deflect the distal end of the catheter; optionally, this may also compress another of the pair of flexible members. The flexible members may have a portion adjacent the distal end with a flattened transverse section, while the balance of the flexible members is circular. A transversely resilient spacer, such as a wave spring, may be disposed between the pair of flexible members.

In yet another embodiment, an electrophysiology/ablation lumen catheter includes: an elongated flexible body having a proximal end and a distal end; at least one electrode disposed adjacent the distal end; a pair of flexible deflection members disposed substantially side-by-side within the body and extending from a point of attachment adjacent the distal end to the proximal end; an inflatable member operatively extending from an outer surface of the body when inflated; a first passage in fluid communication with the inflatable member; a second passage that communicates with an opening in the body, wherein the opening is located distally of the inflatable member; and a handle including an actuator movable in opposite directions and coupled to the pair of flexible deflection members for effecting, upon actuation, longitudinal tensioning of one of the flexible deflection members with respect to the body, thereby effecting lateral displacement of the distal end of the body. A spacer may be provided between the pair of deflection members in order to maintain lateral spacing therebetween, and at least one end of the spacer may be free-floating between the deflection members. The second passage may be dimensioned to receive a medical device, such as a needle or other puncture device, therethrough for introduction into a patient. The opening of the second passage may be located in a sidewall of the body between the tip of the catheter and the inflatable member, or, alternatively, may be located at the tip.

In still another embodiment, an electrophysiology/ablation catheter includes: an elongated flexible body having a proximal end and a distal end; at least one electrode disposed adjacent the distal end; at least one deflection member disposed within the body and extending from a point of attachment adjacent the distal end to the proximal end; an inflatable member operatively extending from an outer surface of the body when inflated; a first passage in fluid communication with the inflatable member; a second passage that communicates with an opening in the body, wherein the opening is located distally of the inflatable member; and a handle including an actuator coupled to the at least one deflection member for effecting, upon actuation, lateral displacement of the distal end of the body.

A primary advantage of the present invention is the ability to combine these various features into a single catheter assembly.

Yet another advantage is the capability of incorporating the inflatable balloon functions in conjunction with a secondary passage for liquid delivery and without impacting the deflection capabilities of the electrophysiology catheter.

A further advantage of the invention relates to alternative use of the liquid delivery passage for placement of a guide wire into a desired heart cavity site.

Still other advantages and benefits of the invention will become apparent to those skilled in the art upon reading and understanding the following detailed description.

DETAILED DESCRIPTION OF THE INVENTION

Figure 1:
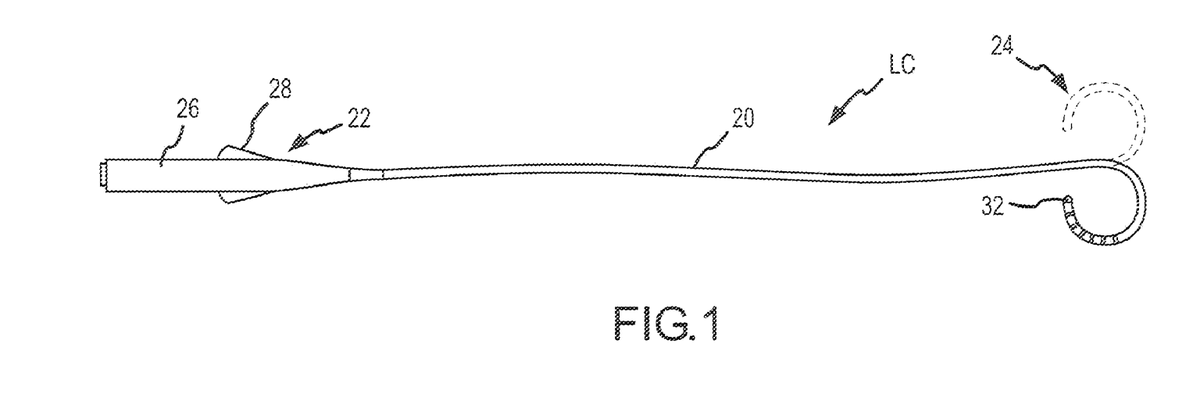
FIG. 1 is a view of the cardiac catheter of the present invention.

FIG. 1 illustrates an electrophysiology lumen catheter LC, and the drawings thereof are not intended to limit the invention. The lumen catheter assembly LC includes an elongated flexible main casing or body 20 that includes an actuator assembly 22 at one end and a distal portion 24 at the other end. Although the details are not shown in FIG. 1, it is also contemplated that the catheter assembly can include two main components, a blood-contacting portion and a sub-assembly that includes the actuator mechanism as shown and described in commonly owned U.S. Pat. No. 5,861,024. The actuator mechanism 22 preferably includes a handle 26 and a delta-shaped (Δ-shaped) actuating member 28 that is selectively manipulated by the user to cause desired deflection or curvature of the distal portion 24 of the catheter assembly. Again, although this particular arrangement of the actuator mechanism and deflectable distal portion are shown and described in the commonly owned prior patents, it will also be appreciated that selective modifications can be made without departing from the scope and intent of the present invention.

Figure 2:
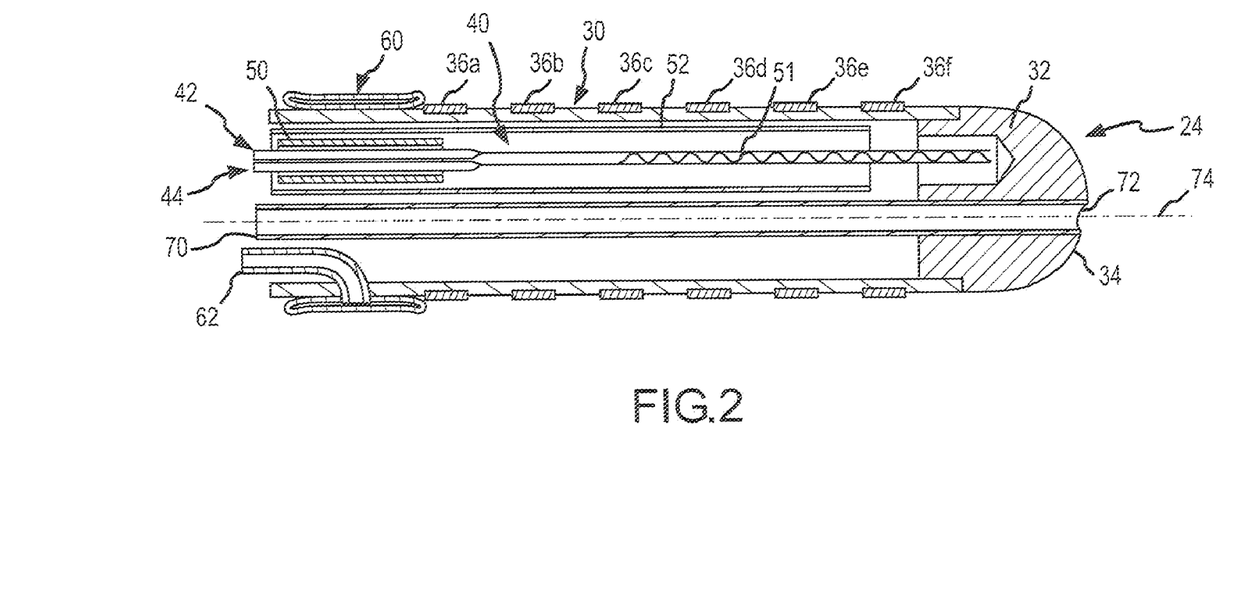
FIG. 2 is an enlarged cross-sectional view of a distal end of a first embodiment of the catheter with an inflatable member in a deflated state.
Figure 3:
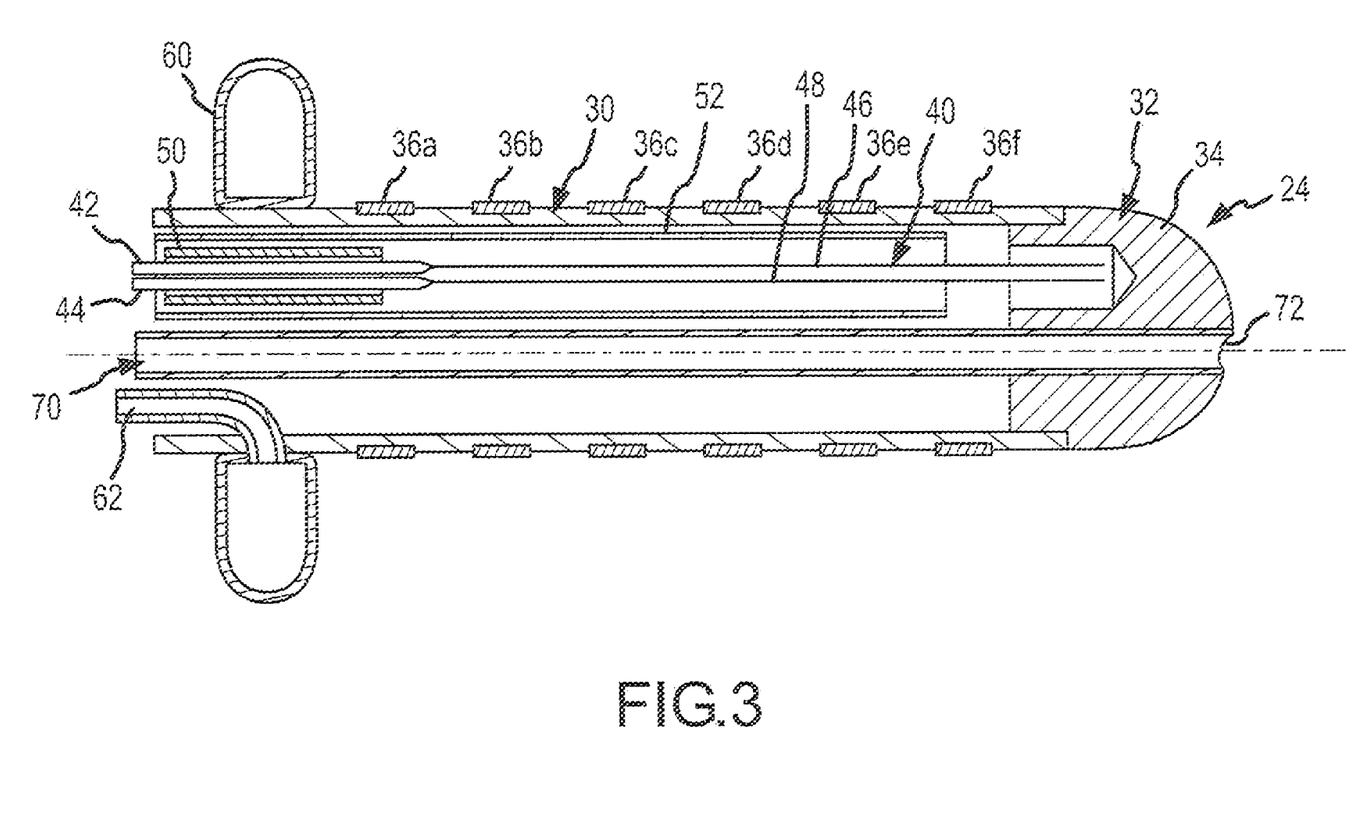
FIG. 3 is a view similar to FIG. 2 with the inflatable member shown in an inflated state.

With continued reference to FIG. 1, and additional reference to FIGS. 2 and 3, a first embodiment of the lumen catheter assembly LC will be described in greater detail. Particularly, the distal portion 24 includes an outer body 30, typically a tubular outer body, that is secured to or receives a distal electrode 32 which is shown as a generally mushroom-shaped configuration. That is, the distal electrode 32 has a hemispherical dome portion 34 that closes the end of the body. In addition, axially spaced electrodes 36a-f are provided along the body 30 and are each connected to a separate electrical wire (not shown for ease of illustration) that conducts electrical energy to the respective electrode in a manner generally well-known in the art for diagnostic and therapeutic procedures.

The distal portion of the catheter is selectively deflected by a catheter deflection assembly. The deflection assembly includes a pair of tension and compression members 40 which acts in concert to selectively deflect the distal end, preferably in a curved configuration (FIG. 1). As particularly illustrated in FIG. 2, the tension/compression member pair 40 includes a first member 42 and a second member 44 disposed in side-by-side relation. The tension/compression members are disposed in side-by-side relation within an inner tube 50 which extends to the proximal end of the catheter (not shown). Additionally, a thin wall polymer tube 52 is received over the flattened ribbon-like portions of the tension/compression members in order to prevent lateral separation of these components during actuation and/or curvature formation. Accordingly, the tube 52 terminates at the location shown in FIG. 2 and does not extend to the proximal end like the inner tube 50. The tension/compression members are typically arranged to provide curved deflection in either direction as represented in phantom in FIG. 1. The tension/compression members are preferably thin wires (e.g., stainless steel wires) received in the tube 50, and include the flattened or ribbon-like portions 46, 48. Optionally, a spacer 51, such as a wave spring, may be disposed between the flattened ends of the tension/compression members 40. Again, particular details of the deflection assembly are shown and described in the commonly assigned patents and applications noted above.

An annular inflatable member such as balloon 60 communicates through a first passage 62 with a source of liquid such as saline. It will be understood that the passage 62 extends through the length of the catheter body and is in operative communication with a liquid source (not shown). As shown in FIG. 2, the annular balloon is disposed on the outer surface of the body 30 and is shown in a deflated condition. Upon introduction of a liquid into the balloon, the balloon inflates to an expanded state or condition (FIG. 3) thereby engaging an inner wall of the body passage and providing a sealed arrangement therewith. The inflatable member is preferably disposed at a predetermined dimension from the terminal end of the distal portion and likewise at a location where the electrodes are interposed between the balloon and the distal tip of the catheter. As will be appreciated, the particular location of the balloon may be varied as desired for particular electrophysiology studies.

Also extending through the body 20 of FIG. 1 is a second lumen or passage 70. The second passage is dimensioned to serve as a liquid or dye delivery tube and also advantageously is dimensioned to alternatively receive a guide wire therethrough for reasons which will be described in greater detail below. The second passage or lumen 70, for example, may have an inner diameter of approximately 0.037 inches, adapting it to receive a guide wire on the order of 0.035 inches. These dimensions are merely for exemplary purposes and should not be deemed limiting, since other dimensions can be used with equal success. The second passage 70 extends the length of the catheter body 20 and preferably terminates at the distal end. As shown in FIGS. 2 and 3, the terminal end or port 72 of this passage is located at the distal tip within the hemispherical dome portion 32. That is, a guide wire, represented herein by dotted line 74, can proceed through the second lumen and facilitates guiding of the distal end of the catheter to a desired location within the body cavity. Thus, it is desirable in this instance that the lumen 70 terminate at the distal tip.

Figure 4:
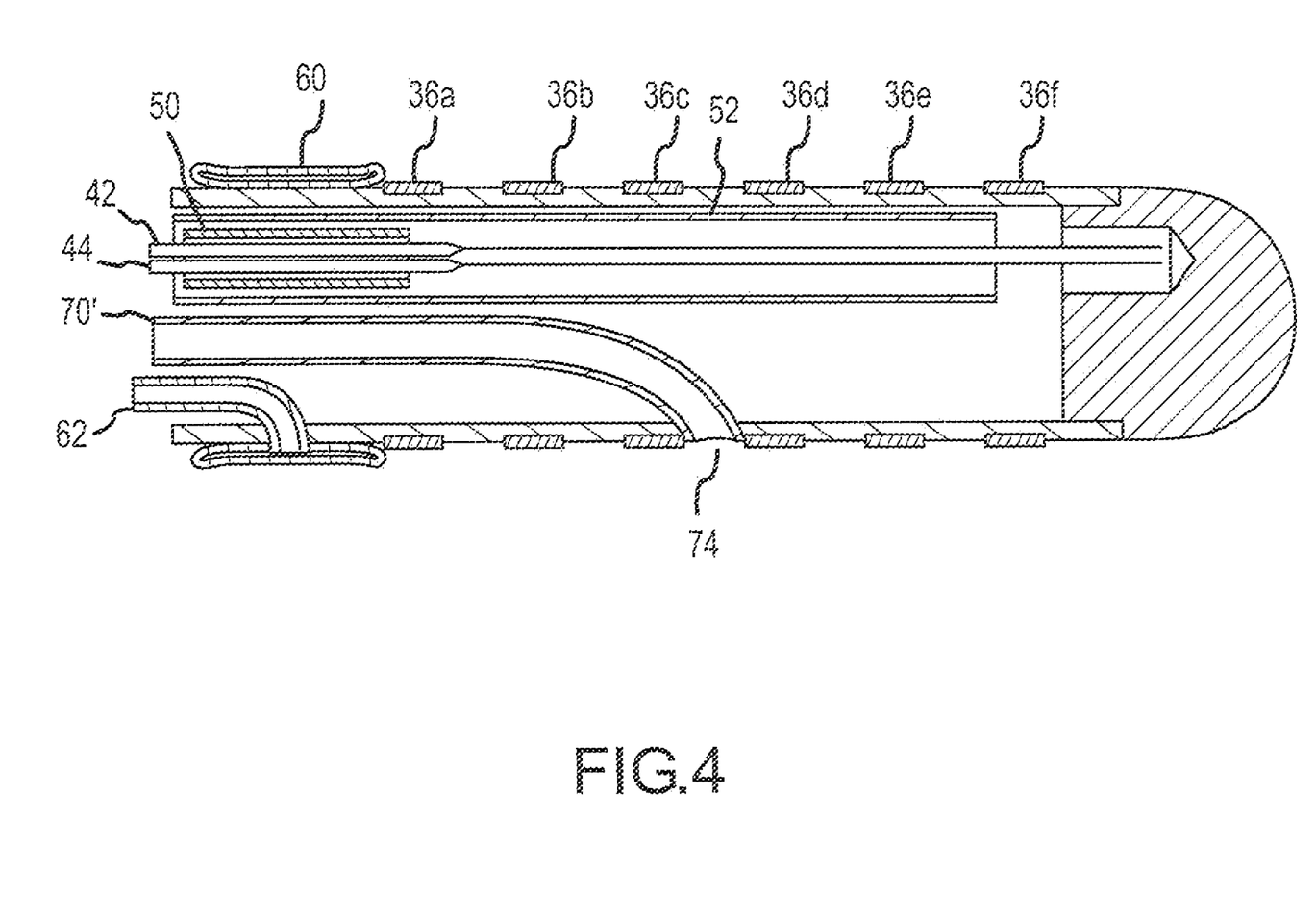
FIG. 4 is an enlarged detail cross-sectional view of a second embodiment of a distal end of the catheter with the inflatable member in a deflated state.
Figure 5:
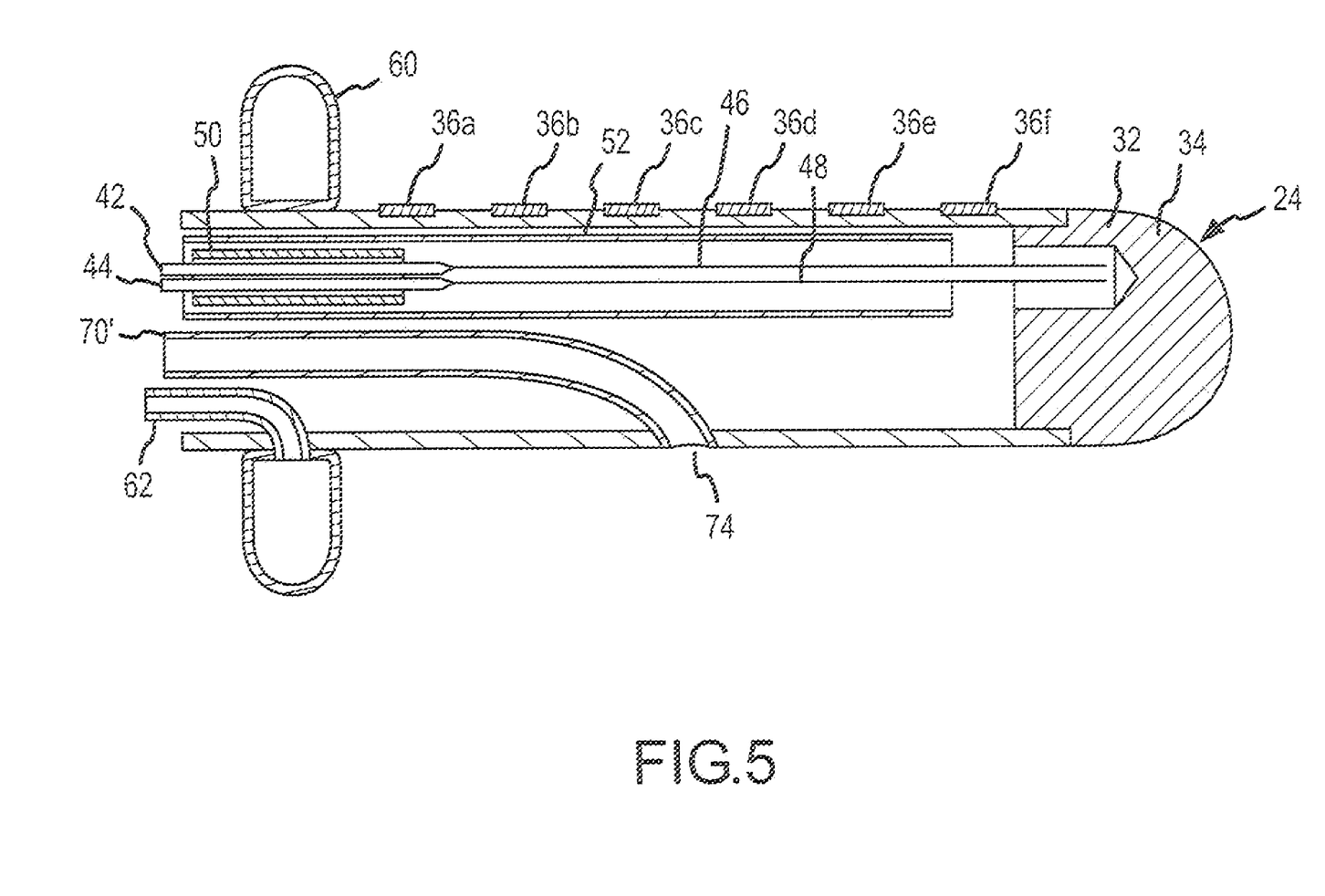
FIG. 5 is a view of the distal portion of the catheter of FIG. 4 with the inflatable member in an inflated state.

This arrangement of the second lumen may be compared to that shown in FIGS. 4 and 5 where like reference numerals with a primed suffix refer to like elements, and new reference numerals refer to new elements. The primary distinction is the location of the terminal end or port of the second passage 70'. Here, the terminal end 74 is located at or extends through a sidewall of the outer body 30. As will be appreciated from FIGS. 4 and 5, the terminal location 74 of the second passage is preferably located between the distal tip and the inflatable member. In this manner, when the balloon is inflated as shown in FIG. 5, the second passage delivers a liquid or dye to a location disposed between the inflated balloon and the distal tip of the catheter. Even though the terminal end of the second passage is not located at the distal tip of the catheter, and may not be as desirable for use as a through passage that receives a guide wire, the embodiment of FIGS. 4 and 5 still provides the advantageous function of a delivery tube through which a liquid or dye can be introduced downstream of the sealed area provided by the inflated balloon (and that is selectively inflated via the first passage 62).

Figure 6:
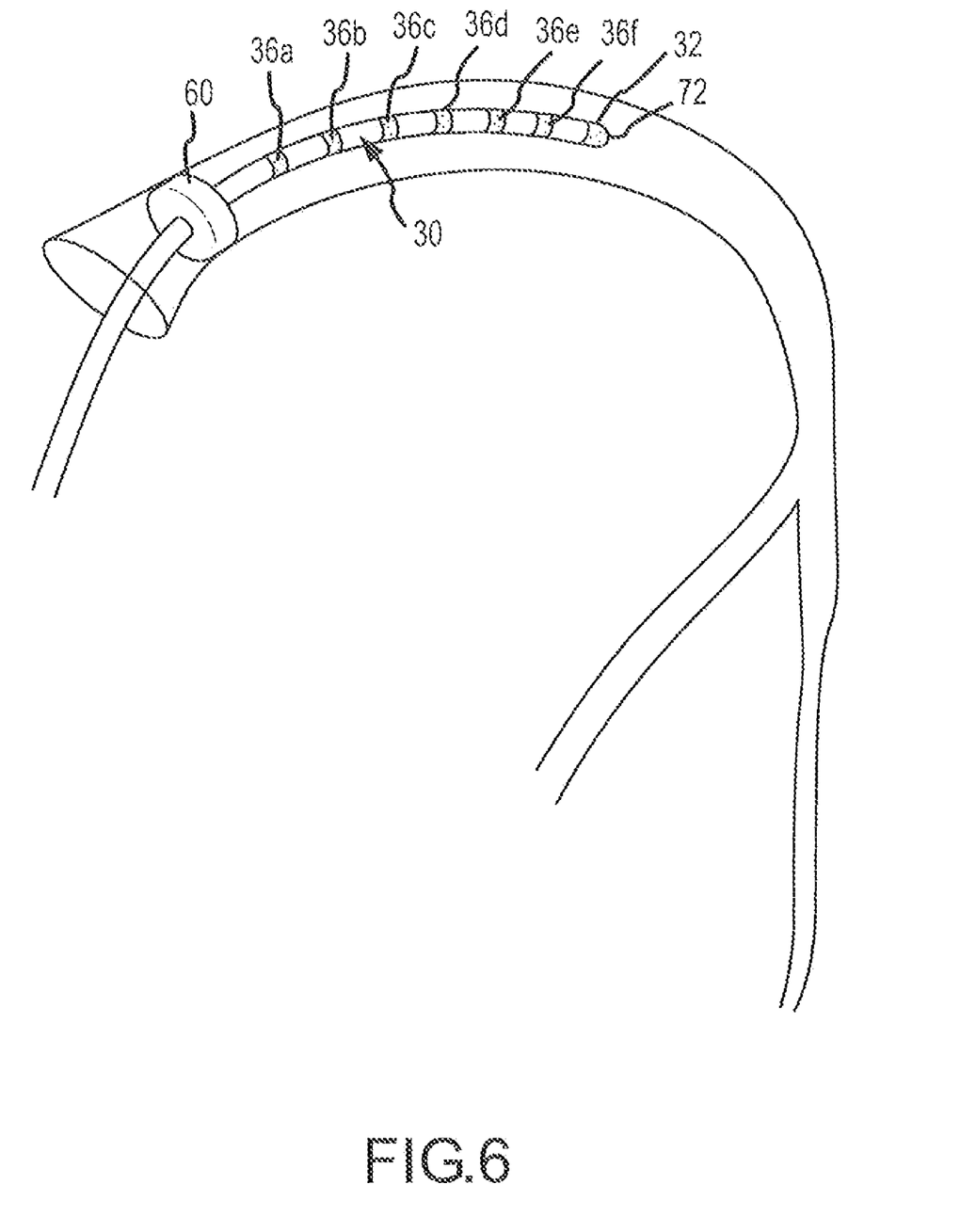
FIG. 6 is a schematic view of the distal portion of the lumen catheter with the inflatable member in an inflated state and liquid being discharged from a port located in the distal end.

As shown in FIG. 6, the distal end of the catheter of FIG. 1 is shown inserted into a cardiac cavity, for example, the coronary sinus. The opening in the coronary sinus is illustrated as a generally conically tapered arrangement. The balloon is inflated into engagement with an interior wall of the coronary sinus passage via a liquid provided through the first passage and fluid is able to be discharged from an end port, whether at the distal end or at another location downstream of the inflated balloon via the second passage, so that the lumen catheter introduces an injected liquid or dye during an electrophysiology study.

In summary, the actuator is still able to alter the configuration of the catheter and the arrangement provides a flexible liquid delivery tube disposed within the catheter shaft. The tip steering mechanism within the catheter handle and distal portion steerability and configuration, along with the electrical features are still retained, while adding the ability to deliver liquid to the cavity of, for example, the heart during cardiac electrophysiology studies. The same second tube may be advantageously used as a passage for placement of a guide wire into a desired site within, for example, the heart cavity. The distal, open end of the secondary passage either exits or terminates at the distal tip of the catheter or at the proximity of the distal tip.

Provision of an inflatable balloon disposed externally and circumferentially in an axi-symmetric configuration on the outer surface of the catheter shaft is provided proximal to the last electrode. Saline or other appropriate liquid may be used to inflate the balloon. The balloon, upon inflation, assumes a preferred annular or donut-shaped configuration. A second flexible tube disposed within the shaft of the catheter has its distal end exiting the catheter outer body and terminating for communication with the interior of the balloon. This allows a second liquid to be introduced into the cavity or to receive a guidewire therethrough.

When the distal portion of the catheter is placed into a typical cardiac vessel for example the coronary sinus, the balloon is inflated in order to prevent backflow of the injected liquid or dye and blood during the electrophysiology study.

Both of the elongated flexible tubes or lumens described above are terminated at the proximal end of the catheter handle with appropriate inlet openings. The openings are used to deliver liquid into each of the tubes as required. When the liquid delivery tube is alternatively used as a passage for guide wire placement, the guide wire can be introduced into this tube via its inlet opening, positioned at the proximal end of the catheter. Once the catheter distal end is positioned in place, the guidewire is then removed and the lumen can be used to introduce a liquid into the body cavity.

Although several embodiments of this invention have been described above with a certain degree of particularity, those skilled in the art could make numerous alterations to the disclosed embodiments without departing from the spirit or scope of this invention. For example, one of ordinary skill in the art will appreciate that, in addition to introducing a guide wire through second passage 70, one may introduce another medical device, such as a needle or other puncture device, therethrough.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An electrophysiology/ablation lumen catheter, comprising:
   a) an elongated flexible body having a central lumen, a proximal end and a series of spaced electrodes disposed adjacent a distal end thereof;
   b) a pair of tension/compression members extending through the body for selectively deflecting at least the distal end of the body;
   c) an electrical lead connected to each of the electrodes and extending through the body to adjacent the proximal end thereof, the leads adapted for external connection thereof;
   d) an actuator operatively connected to the tension/compression members and operable upon movement to effect lateral displacement of the distal end;
   e) an inflatable member operatively extending from an outer surface of the body when inflated;
   f) a first passage extending through the body within said central lumen and adapted to supply an associated liquid therethrough to the inflatable member; and
   g) a second passage within said central lumen that communicates with an opening in the body located on a distal end side of the inflatable member.

2. The lumen catheter of claim 1, wherein the second passage is adapted to convey an associated fluid from the proximal end of the catheter to the distal end and into an associated body cavity.

3. The lumen catheter of claim 1, wherein the opening is located at a terminus/tip of the distal end.

4. The lumen catheter of claim 1, wherein the opening is located inwardly from a terminus of the distal end.

5. The lumen catheter of claim 1, wherein the opening is axially located between a terminus of the distal end and the inflatable member.

6. The lumen catheter of claim 1, wherein the second passage is dimensioned to receive a guidewire therethrough.

7. An electrophysiology/ablation lumen catheter, comprising:
   a) an elongated flexible body having a central lumen, a proximal end and at least one electrode disposed adjacent a distal end thereof;
   b) a catheter deflection assembly disposed in the body, wherein the catheter deflection assembly includes a pair of flexible members disposed substantially side-by-side within said body;
   c) an electrical lead connected to each of the at least one electrodes and extending through the body;
   d) an actuator connected adjacent the proximal end of the elongated flexible body and operable upon movement to effect displacement of the distal end through the catheter deflection assembly;
   e) an inflatable member operatively extending from an outer surface of the body when inflated;
   f) a first passage extending through the body within said central lumen and adapted to supply a first fluid therethrough to the inflatable member; and
   g) a second passage within said central lumen that terminates at an opening in the body located on a distal end side of the inflatable member.

8. The lumen catheter of claim 7, wherein the second passage is adapted to convey a second fluid from the proximal end of the catheter to the distal end and to discharge the second fluid outside the body of the lumen catheter.

9. The lumen catheter of claim 7, wherein the opening is located at a terminus of the distal end.

10. The lumen catheter of claim 7, wherein the opening is located inwardly from a terminus of the distal end.

11. The lumen catheter of claim 7, wherein the pair of flexible members extend through the body from a point of attachment adjacent the distal end to the proximal end.

12. The lumen catheter of claim 7, wherein the catheter deflection assembly moves the distal end in a plane substantially normal to a longitudinal extent of the catheter.

13. The lumen catheter of claim 7, wherein tensioning of one of the pair of flexible members deflects the distal end of the catheter.

14. The lumen catheter of claim 13, wherein tensioning of one of the pair of flexible members compresses the other of the pair of flexible members.

15. The lumen catheter of claim 7, wherein the pair of flexible members each have a portion thereof adjacent the distal end formed to have a flattened transverse section with the balance thereof circular.

16. The lumen catheter of claim 7, further comprising a transversely resilient spacer disposed between the pair of flexible members adjacent the distal end of the catheter.

17. The lumen catheter of claim 7, wherein the second passage is dimensioned to receive a guidewire therethrough.

18. An electrophysiology/ablation lumen catheter, comprising:
   an elongated flexible body having a central lumen, a proximal end and a distal end;
   at least one electrode disposed adjacent the distal end;
   a pair of flexible deflection members disposed substantially side-by-side within the body and extending from a point of attachment adjacent the distal end towards the proximal end;
   an inflatable member operatively extending from an outer surface of the body when inflated;
   a first passage within said central lumen and coupled to the inflatable member by which the inflatable member may be filled with a fluid;
   a second passage within said central lumen that terminates at an opening in the body, wherein the opening is located distally of the inflatable member; and
   a handle including an actuator movable in opposite directions and coupled to the pair of flexible deflection members for effecting, upon actuation, longitudinal tensioning of one of the flexible deflection members with respect to the body, thereby effecting deflection of the distal end of the body.

19. The catheter according to claim 18, further comprising a spacer disposed between the pair of flexible deflection members and configured to maintain lateral spacing therebetween, at least one end of the spacer floating freely between the pair of flexible deflection members.

20. The catheter according to claim 18, wherein the second passage provides a fluid path for a fluid to flow through the opening and exit the lumen catheter.

21. The catheter according to claim 18, wherein the second passage is dimensioned to receive a medical device therethrough, such that the medical device may be introduced into a patient.

22. The catheter according to claim 18, wherein the second passage is dimensioned to receive a needle therethrough, such that the needle may be introduced into a patient.

23. The catheter according to claim 18, wherein the opening is located in a sidewall of the body between the inflatable member and the distal end.

24. The catheter according to claim 18, wherein the opening is located at the distal end of the body.

* * * * *